United States Patent [19]

Hsu

[11] Patent Number: 5,028,620

[45] Date of Patent: Jul. 2, 1991

[54] BIOCIDE COMPOSITION

[75] Inventor: Jemin C. Hsu, Fort Washington, Pa.

[73] Assignee: Rohm and Haas Company, Philadelphia, Pa.

[21] Appl. No.: 244,771

[22] Filed: Sep. 15, 1988

[51] Int. Cl.5 .................... A01N 43/78; A61K 31/425
[52] U.S. Cl. ..................................... 514/372; 424/405
[58] Field of Search .................. 424/405, 78; 514/372; 523/122

[56] References Cited

U.S. PATENT DOCUMENTS 3,761,488  9/1973  Lewis et al. .
3,769,315  10/1973  Keener et al. .
3,929,561  12/1975  Shema et al. ........................ 514/372
4,150,026  4/1979  Miller et al. .
4,396,413  8/1983  Miller et al. .
4,454,146  6/1984  Borovian ............................. 514/372
4,505,889  3/1985  Amick .
4,661,503  4/1987  Martin et al. ......................... 514/372
4,732,905  3/1988  Donofuo et al. ..................... 514/372

OTHER PUBLICATIONS

Kathon Biocide: Manifestation of Delayed Contact Dermatitis in Guinea Pigs is Dependent on the Concentration for Induction and Challenge—The Journal of Investigative Dermatology, 81:409–411, 1983.

Primary Examiner—John Doll
Assistant Examiner—Pili Curtis
Attorney, Agent, or Firm—Michael B. Fein

[57] ABSTRACT

This invention relates to synergistic biocide compositions having decreased sensitization potential.

3 Claims, No Drawings

BIOCIDE COMPOSITION

This invention relates to biocide compositions of 5-chloro-2-methyl-4-isothiazolin-3-one and 2-methyl-4-isothiazolin-3-one (also known as 5-chloro-2-methyl-3-isothiazolone and 2-methyl-3-isothiazolone, respectively) which at specific use levels exhibit not only synergy but also exhibit a much lower incidence of sensitization.

The search for ways to lower sensitization to biocides is a continuing one. All or nearly all commercially available preservatives possess skin sensitization potential.

The biocides and their preparations are disclosed in U.S. Pat. Nos. 3,761,488; 4,150,026; 4,396,413; 4,505,889 and 3,769,315.

Kathon biocide (886) a widely used, broad spectrum antimicrobial agent, contains, as active ingredients (a.i.), a mixture of 5-chloro-2-methyl-4-isothiazolin-3-one ("651") and 2-methyl-4-isothiazolin-3-one ("573") in an approximate ratio of 3:1, respectively, with magnesium chloride (9%) and magnesium nitrate (16%) present as stabilizers. The biocide is an effective preservative for toiletry formulations, cosmetic and household cleaning products. It is also used in some heavy industrial applications such as cooling-tower water, metalworking fluid, and latex emulsions.

A variety of industrial chemicals, cosmetic fragrances, and therapeutic agents, as well as several naturally occurring substances such as poison ivy, can cause delayed contact dermatitis in animals and humans. These sensitizers fall into diversified chemical categories ranging from simple inorganic metals, such as nickel, to complex organic chemicals.

Several articles on the description of how tests are conducted and which relate to isothiazolones are: "Demonstration of Kathon ® CG in some commercial products", Contact Dermatitis 1986: 15: 24-27; "Allergic contact dermatitis due to a biocide containing 5-chloro-2-methyl-4-isothiazolin-3-one", Contact Dermatitis 1986: 14: 201-204; "Patch test sensitivity to Kathon ® CG", Contact Dermatitis 1986: 14: 155-157; "Contact allergy to the preservative Kathon ® CG", Contact Dermatitis 1986: 14: 85-90; "Immediate and delayed reactions to cosmetic ingredients", Contact Dermatitis 1985: 13: 258-265; "Diagnostic patch test concentration for Kathon CG", Contact Dermatitis 1985: 13: 242-245; "Biocide patch tests", Contact Dermatitis 1985: 12: 99-103; and "Patch tests with fragrance materials and preservatives", Contact Dermatitis 1985: 12: 87-92.

In the effort to find a way to decrease sensitization while keeping the effectiveness at an acceptable level it was found that it is possible to use specific combinations of 651 and 573 which decrease the sensitization by a factor of about 15 to 20 while decreasing the activity by a factory of only about 3. It was further discovered that the composition demonstrated unexpected activity between various use rates.

The invention relates specifically to a microbicidal composition, which has the same uses as the present commercial isothiazolones, comprising a synergistic mixture the first component of which is 5-chloro-2-methyl-4-isothiazolin-3-one (651) and the second component of which is 2-methyl-4-isothiazolin-3-one (573). The synergistic compositions have from about 1.2 to about 25.4% of 5-chloro-2-methyl-4-isothiazolin-3-one (651) with the amount of from about 2.3 to about 8.5% of 651 being preferred and an amount of from about 2.3 to about 4.5% of 651 being most preferred.

The invention also relates to a method of inhibiting the growth of bacteria, fungi or algae in a locus subject to contamination by bacteria, fungi or algae, which comprises incorporating into or onto the locus in an amount which is effective to adversely affect the growth of bacteria, fungi or algae the synergistic combination of 651 and 573.

The composition of the invention can be formulated as solutions in water. While the amount of the instant composition in the formulated solution can vary over a wide range, the solutions can conveniently be formulated to contain from about 20 to about 100 ppm of the composition in solution, with the preferred range being from about 25 to 50 ppm of the composition. In formulating the solutions, other solvents which are water-miscible, such as ethyl alcohol, propyl alcohol, isopropyl alcohol, diethylene glycol, dipropylene glycol, polyethylene glycol, diethylene glycol ethyl ether, and the like, may be employed in order to aid in solubizing the active components. Furthermore, various other conventional additives may be employed, such as surfactants, dispersing agents, corrosion inhibitors, and the like.

Potential areas of general application of these synergistic combinations include disinfectants, sanitizers, cleaners, deodorizers, liquid and powder soaps, skin removers, oil and grease removers, food processing chemicals, dairy chemicals, food preservatives, animal food preservatives, wood preservation, aqueous dispersions of organic polymers, paint, lazures, stains, mildewcides, hospital and medical antiseptics, metal working fluids, cooling water, air washers, petroleum production, paper treatment, paper mill slimicides, petroleum products, adhesives, textiles, pigment slurries, latexes, leather and hide treatment, petroleum fuel, heating oil, laundry sanitizers, agricultural formulations, inks, mining, nonwoven fabrics, petroleum storage, rubber, sugar processing, tobacco, swimming pools, cosmetics, toiletries, pharmaceuticals, chemical toilets, household laundry products, diesel fuel additives, waxes and polishes and many other applications where water and organic materials come in contact under conditions which allow the growth of undesired microorganisms.

Other known biocides may be combined advantageously with the isothiazolones of this invention to afford a biocide having broader activity.

The products of this invention are especially useful as preservatives for products which may be in contact with the skin such as cosmetics, toiletries and the like.

The synergistic 573/651 combinations provide long-lasting activity for controlling a wide spectrum of microorganisms at a small fraction of concentrations needed by either 573 or 651 alone.

PREPARATION OF COMBINATIONS

The following examples illustrate the preparation of the combinations. They can be prepared by starting with substantially pure 651 and 573 or by adding substantially pure 573 to 886.

EXAMPLE 1

To 179 g monochlorobenzene (MCB) were co-fed chlorine and a 25% solution of N-methyl-3-mercaptopropionamide (MMPA) in MCB at a molar ratio of about 1.4 in about 105 minutes at 50° C. with a good mixing till 1.5 mole MMPA was fed. At the end of co-feed, the chlorine feed was continued to a final molar feed ratio of 2.0.

The chlorination slurry was filtered, washed with an appropriate solvent and dried to afford the hydrochloride salt of:

| | |
|---|---|
| 573 = | 61.3% |
| 651 = | 2.74% |
| Ratio = | 95.7:4.3 |

The above hydrochloride product was slurried in water and was neutralized to pH 4 by adding gradually solid sodium carbonate. The solution was filtered to obtain the product containing:

| | |
|---|---|
| 573 = | 28.8% |
| 651 = | 1.2% |
| Ratio = | 96:4 |

EXAMPLE 2

To a stirred 1.0 mole solution of 25% MMPA in MCB was passed 1 mole anhydrous hydrogen chloride at 45° C. in 1 hour. Next the mixture was chlorinated by adding 2 moles of chlorine over a period of 2.5 hours while agitating and maintaining the batch temperature around 45° C. At the end of chlorination, the mixture was degassed for 20 minutes to remove free hydrogen chloride. The chlorination slurry was then filtered, washed with MCB and dried to afford the hydrochloride salt of:

| | |
|---|---|
| 573 = | 60.4% |
| 651 = | 3.0% |

The above hydrochloride salt was slurried in water and neutralized to pH 6.5 by gradually adding sodium bicarbonate powder at 20° C. to afford an aqueous solution of product:

| | |
|---|---|
| 573 = | 29.8% |
| 651 = | 1.5% |
| Ratio = | 95.2:4.8 |

EXAMPLE 3

By employing the method used in Example 1, but by substituting MMPA with an equimolar quantity of pure N,N'-Dimethyldithiodipropionamide and co-feeding chlorine at a molar ratio of 2.25, and continuing chlorine feed to a final molar feed ratio of 3.0, afforded the hydrochloride product:

| | |
|---|---|
| 573 = | 60.3% |
| 651 = | 3.2% |
| Ratio = | 95:5 |

The hydrochloride product was neutralized as in Example 1 above to afford an aqueous solution with the 573:651 ratio of 95:5.

EXAMPLE 4

By employing the method used in Example 2 above, but substituting MMPA with an equimolar quantity of pure N,N'-dimethyldithiodipropionamide and adding 3 equivalents of chlorine instead of 2 equivalents, there is obtained the hydrochloride salt, which was filtered, washed and reslurried in water. The aqueous slurry was neutralized to afford the aqueous product with the following composition:

| | |
|---|---|
| 573 = | 30.5% |
| 651 = | 0.9% |
| Ratio = | 97:3 |

EXAMPLE 5

The filtered and washed chlorination slurry from Example 4 was reslurried in an appropriate solvent and neutralized with anhydrous ammonia. The ammonium chloride was filtered off and washed with the solvent. The filtrate and washing were combined and stripped (35°/10 mm Hg) to afford the combination containing 92.1% of 573 and 4.8% of 651. (Ratio=95:5.)

EXAMPLE 6

By dissolving 1.45 g of substantially pure 573 (see example 7) and 0.045 g of 886 in 98 g water a combination of the following composition is prepared:

| | |
|---|---|
| 573 = | 1.466% |
| 651 = | 0.055% |
| Ratio = | 96.4:3.6 |

EXAMPLE 7

Preparation of substantially pure 573 solution

The hydrochloride obtained in Example 1 was dissolved in 500 g of boiling methanol and gradually cooled to 10° C. The crystal slurry was filtered and washed with cool solvent and dried in vacuum to afford 132.8 g of 573 hydrochloride containing 74.9% free base and 24.1% HCl (99.0%) with no 651.

45 g of the above hydrochloride salt was dissolved in 135 g water and neutralized to pH 4.2 by adding a 20% aqueous sodium carbonate solution to afford an aqueous solution containing:

573=12.5%
651=<0.1%   4,5dichloro-2-methyl-4-isothiazolin-3-one=<0.1

EXAMPLE 8

Preparation of substantially pure 573

The slurry of 354 g (1.5 moles) of N,N'-dimethyldithiodipropionamide in 2 l. butyl acetate was cooled to −20° C., and under its surface was passed 335 g (4.72 moles, 3.14 equiv.) of chlorine over a period of 100 minutes. The mixture was allowed to warm to 15° C. when an exchange reaction occurred. The batch was held below 50° C. and allowed to stand at room temperature for 1 hour. Next, the mixture was filtered and the wet cake washed with 200 ml butyl acetate and dried in vacuum. The 472 g crude hydrochloride salt was recrystallized from methanol to afford substantially pure 573 hydrochloride salt (99%).

This was dissolved in water and neutralized with potassium carbonate to a pH 7.5 to afford a 25.0% product solution.

The above solution was extracted with ethylene dichloride (EDC, 1×800 ml, 2×300 ml). The EDC extracts were combined and the solvent removed to afford 241 g of 99.7% pure 573.

EXAMPLE 9

Preparation of substantially pure 651

A chlorination slurry obtained by the chlorination of N-methyl-3-mercaptopropionamide in toluene by co-feeding it with chlorine at a molar feed ratio of 3.0 was filtered, washed and dried to afford a hydrochloride salt containing:

| | |
|---|---|
| 573 = | 19.8% |
| 651 = | 57.8% |
| Ratio = | 25.5:74.5 |

The hydrochloride salt, (225 g), was slurried in 870 ml of ethyl ether and to it was added dropwise 54.3 g of pyridine (0.686 moles, the amount required to neutralized 80% of 651 hydrochloride). The mixture was filtered and the solids washed with ethyl ether. The filtrate and washings were combined and stripped (35°/20mm Hg) to afford 90 g of pale yellow crystalline solids containing 98.5% 651.

EVALUATION OF SYNERGY

The synergism of the combinations is demonstrated by testing at a wide range of concentrations and ratios of the two components generated by 2-fold serial dilutions in a growth medium (Trypticase Soy Broth or TSB, Difco) of 573 in one dimension and 886 in a second dimension, against a mixture of the following 12 microorganisms: *Escherichia coli* (ATCC 11229) *Candida albicans* (ATCC 11651), *Pseudomonas oleovarans* (ATCC 8062), *Pseudomonas aeruginosa* (ATCC 15442), *Staphylococcus aureus* (ATCC 6538), *Enterobacter aerogenes* (ATCC 15038), *Pseudomonas cepacia* (ATCC 17765), *Pseudomonas putida* (ATCC 795), *Aspergillus niger* (ATCC 6275), *Talaromyces luteus* (ATCC 10465), *Penicillum oxalicum* (ATCC 24784) and *Serratia marcescens* (a shampoo isolate). Each single culture was inoculated to TSB agar slants and incubated for 2 days at 30° C. for *C. albicans* and all bacteria except *E. coli* and *S. aureus*, which were at 37° C., and incubated for 10-14 days at 25° C. for fungal cultures. The bacteria and fungi were then washed off the slants with phosphate buffer (0.125 M, pH 7.2) and inoculated into each test tube containing a given concentration and ratio of 573 and 886 to make final cell concentration of about $2 \times 10^7$ bacteria and $2 \times 10^6$ fungi per ml. The lowest concentration of the two components, acting alone or in a mixture, to visibly inhibit cell growth at 30° C. for over 7 days is the minimum inhibitory concentration (MIC). Seven days after inoculation, 5 microliter of sample from each test tube (containing about $10^5$ bacteria and $10^4$ fungi from original inoculation) was removed and assessed for viable organisms by 1:50 dilution into TSB medium and checked for regrowth. No viable organisms were detected from the test tubes where MICs were observed Thus, the MICs showed very good control of those organisms and were taken as end points of activity. Each test tube was reinoculated 2 more times (a total of 3 inoculations) to determine the capacity and the long-lasting activity of the combinations.

TABLE 1

| Treatments (ppm) | | | Experiment No. 1 Growth after inoculation | | | Experiment No. 2 Growth after inoculation | | |
|---|---|---|---|---|---|---|---|---|
| 573 (A) | 886 (B) | Ratio A/B | 1st | 2nd | 3rd | 1st | 2nd | 3rd |
| 500.0 | 0.0 | 0 | − | − | − | − | − | − |
| 250.0 | 0.0 | 0 | − | + | + | − | − | − |
| 125.0 | 0.0 | 0 | + | + | + | − | − | − |
| 62.5 | 0.0 | 0 | + | + | + | + | + | + |
| 31.2 | 0.0 | 0 | + | + | + | + | + | + |
| 15.6 | 0.0 | 0 | + | + | + | + | + | + |
| 9.8 | 0.0 | 0 | + | + | + | + | + | + |
| 3.9 | 0.0 | 0 | + | + | + | + | + | + |
| 2.0 | 0.0 | 0 | + | + | + | + | + | + |
| 1.0 | 0.0 | 0 | + | + | + | + | + | + |
| 0.5 | 0.0 | 0 | + | + | + | + | + | + |
| 250.0 | 0.3 | 1000 | − | + | + | − | − | − |
| 250.0 | 0.5 | 500 | − | − | + | − | − | − |
| 125.0 | 0.3 | 500 | + | + | + | − | − | − |
| 250.0 | 1.0 | 250 | − | − | − | − | − | − |
| 125.0 | 0.5 | 250 | − | + | + | − | − | − |
| 62.5 | 0.3 | 250 | + | + | + | + | + | + |
| 250.0 | 2.0 | 125 | − | − | − | − | − | − |
| 125.0 | 1.0 | 125 | − | + | + | − | − | − |
| 62.5 | 0.5 | 125 | + | + | + | + | + | + |
| 31.2 | 0.3 | 125 | + | + | + | + | + | + |
| 250.0 | 4.0 | 62.5 | − | − | − | − | − | − |
| 125.0 | 2.0 | 62.5 | − | − | − | − | − | − |
| 62.5 | 1.0 | 62.5 | + | + | + | − | − | − |
| 71.2 | 0.5 | 62.5 | + | + | + | + | + | + |
| 15.6 | 0.3 | 62.5 | + | + | + | + | + | + |
| 250.0 | 8.0 | 31.2 | − | − | − | − | − | − |
| 125.0 | 8.0 | 31.2 | − | − | − | − | − | − |
| 62.5 | 2.0 | 31.2 | − | − | − | − | − | − |
| 31.2 | 1.0 | 31.2 | + | + | + | − | − | − |
| 15.6 | 0.5 | 31.2 | + | + | + | + | + | + |
| 7.8 | 0.3 | 31.2 | + | + | + | + | + | + |
| 250.0 | 16.0 | 15.6 | − | − | − | − | − | − |
| 125.0 | 8.0 | 15.6 | − | − | − | − | − | − |
| 62.5 | 4.0 | 15.6 | − | − | − | − | − | − |
| 31.2 | 2.0 | 15.6 | − | − | − | − | − | − |
| 15.6 | 1.0 | 15.6 | + | + | + | + | + | + |
| 7.8 | 1.5 | 15.6 | + | + | + | + | + | + |

TABLE 1-continued

| Treatments (ppm) | | Ratio A/B | Experiment No. 1 Growth after inoculation | | | Experiment No. 2 Growth after inoculation | | |
|---|---|---|---|---|---|---|---|---|
| 573 (A) | 886 (B) | | 1st | 2nd | 3rd | 1st | 2nd | 3rd |
| 3.9 | 0.3 | 15.6 | + | + | + | + | + | + |
| 125.0 | 16.0 | 8 | − | − | − | − | − | − |
| 62.5 | 8.0 | 8 | − | − | − | − | − | − |
| 31.2 | 4.0 | 8 | − | − | − | − | − | − |
| 15.6 | 2.0 | 8 | − | + | + | − | + | + |
| 7.8 | 1.0 | 8 | + | + | + | + | + | + |
| 3.9 | 0.5 | 8 | + | + | + | + | + | + |
| 2.0 | 0.3 | 8 | + | + | + | + | + | + |
| 62.5 | 16.0 | 4 | − | − | − | − | − | − |
| 31.2 | 8.0 | 4 | − | − | − | − | − | − |
| 15.6 | 4.0 | 4 | − | + | + | − | + | + |
| 7.8 | 2.0 | 4 | − | + | + | + | + | + |
| 3.9 | 1.0 | 4 | + | + | + | + | + | + |
| 2.0 | 0.5 | 4 | + | + | + | + | + | + |
| 1.0 | 0.3 | 4 | + | + | + | + | + | + |
| 31.2 | 16.0 | 2 | − | − | − | − | − | − |
| 15.6 | 8.0 | 2 | − | − | + | − | + | + |
| 7.8 | 6.0 | 2 | − | + | + | − | + | + |
| 3.9 | 2.0 | 2 | + | + | + | + | + | + |
| 2.0 | 1.0 | 2 | + | + | + | + | + | + |
| 1.0 | 0.5 | 2 | + | + | + | + | + | + |
| 0.5 | 0.3 | 2 | + | + | + | + | + | + |
| 15.6 | 16.0 | 1 | − | − | − | − | − | + |
| 7.8 | 8.0 | 1 | − | + | + | − | + | + |
| 3.9 | 6.0 | 1 | − | + | + | + | + | + |
| 2.0 | 2.0 | 1 | + | + | + | + | + | + |
| 1.0 | 1.0 | 1 | + | + | + | + | + | + |
| 0.5 | 0.5 | 1 | + | + | + | + | + | + |
| 7.8 | 16.0 | 0.5 | − | + | + | − | + | + |
| 3.9 | 8.0 | 0.5 | − | + | + | + | + | + |
| 2.0 | 4.0 | 0.5 | + | + | + | + | + | + |
| 1.0 | 2.0 | 0.5 | + | + | + | + | + | + |
| 0.5 | 1.0 | 0.5 | + | + | + | + | + | + |
| 3.9 | 16.0 | 0.25 | − | + | + | − | + | + |
| 2.0 | 8.0 | 0.25 | − | + | + | + | + | + |
| 1.0 | 4.0 | 0.25 | + | + | + | + | + | + |
| 0.5 | 2.0 | 0.25 | + | + | + | + | + | + |
| 2.0 | 16.0 | 0.13 | − | + | + | − | + | + |
| 1.0 | 8.0 | 0.13 | + | + | + | + | + | + |
| 0.5 | 4.0 | 0.13 | + | + | + | + | + | + |
| 1.0 | 16.0 | 0.06 | − | + | + | − | + | + |
| 0.5 | 8.0 | 0.06 | + | + | + | + | + | + |
| 0.5 | 16.0 | 0.03 | − | + | + | − | + | + |
| 0.0 | 32.0 | 0 | − | − | − | − | − | − |
| 0.0 | 16.0 | 0 | − | + | + | − | + | + |
| 0.0 | 8.0 | 0 | + | + | + | + | + | + |
| 0.0 | 4.0 | 0 | + | + | + | + | + | + |
| 0.0 | 2.0 | 0 | + | + | + | + | + | + |
| 0.0 | 1.0 | 0 | + | + | + | + | + | + |
| 0.0 | 0.5 | 0 | + | + | + | + | + | + |
| 0.0 | 0.3 | 0 | + | + | + | + | + | + |
| 0.0 | 0.0 | 0 | + | + | + | + | + | + |

− growth inhibited
+ growth not inhibited

Synergism is determined by the industrially accepted method described by Kull, F.C.; Eisman, P.C.; Sylvestrowicz, H.D. and Mayer, R.L. in *Applied Microbiology* 9:538–541 (1961) using the ratio determined by $$\frac{Qa}{QA} + \frac{Qb}{QB} = \text{Synergy Index (SI)}$$

wherein

QA = concentration of compound A in parts per million (ppm), acting alone, which produced an end point
Qa = concentration of compound A in ppm, in the mixture, which produced an end point
QB = concentration of compound B in ppm, acting alone, which produced an end point
Qb = concentration of compound B in ppm, in the mixture, which produced an end point When the sum of Qa/QA plus Qb/QB is greater than one, antagonism is indicated. When the sum is equal to one, additivity is indicated, and when the sum is less than one, synergism is indicated.

The test results for demonstration of synergism between 573 and 651 are shown in Table 1. As shown, a wide range of concentration and ratios was tested. More importantly all the critical end-point activities for the combinations were covered. The combinations that consistently provide control for all three inoculations are considered most effective. Thus, the end-point activities are based on the minimum concentrations of a given ratio of combination product that inhibit all three inoculations.

Table 2 shows the calculation of synergism between 573 and 651 combinations. The end-point activity (MIC in ppm) is taken from Table 1.

QA is the end-point activity of 573 alone
QB is the end-point activity of 886 alone Qa is the end-point activity 573 in the mixture of 573 and 886

Qb is the end-point activity of 886 in the mixture of 573 and 886.

Since 886 is 25% 573 and 75% 651, the total 573 (Qa') in the combinations is Qa +25% Qb, and the total 651 (Qb') in the combinations is 75% Qb. Total concentration of 573 and 651 in the mixture is Qa' and Qb' The % 573 in the mixture is Qa'/(Qa'+Qb'), and %651 in the mixture is Qb'/(Qa'+Qb'.)

Calculation of the synergy index (SI) for 573 and 651 combinations is based on data in Table 1 that shows 573, at very low concentrations (<8 ppm), does not contribute significantly to the overall activity of 886. In other words, the activity of 886 at most recommended use rates (<30 ppm) is essentially the activity of 651. Therefore, the calculation of synergy index (SI) is Qa'/QA +Qb'/0.75 QB. The most preferred synergy for 573 and 651 combinations is seen at 2.3%-4.5% of 651. Taking the synergy index of less than 0.5 as most significant, then a range of 2.3% to 8.5% of 651 in the 573/651 combinations is preferred.

The following Table 2 shows the end-points and the results of the calculations.

sensitization potential of 886 (containing 75% 651 and 25% 573) and pure 573.

These results are reported in Table 3.

The closed-patch test of Buehler *Current Concepts in Cutaneous Toxicology*, (New York: Academic Press 1970), pp. 25–40, is used to investigate the sensitization potential of the materials in the guinea pig. The combination (1.5% total active ingredient) at aqueous concentrations of 1000, 5000, 10000 and 15000 ppm a.i., the 886 (13.9% total active ingredient) at aqueous concentrations of 250, 500 and 750 ppm a.i. and the 573 (solid containing 99.5% total active ingredient) at aqueous concentrations of 5000, 15000 and 30000 ppm a.i. were applied topically to the skin of guinea pigs by means of occluded patches (0.4 ml per patch). All guinea pigs (10 per group at each concentration) received a total of ten 6-hr induction exposures over a 22 day period. In addition, a group of guinea pigs were treated with dry patches only and served as the naive control group. Two weeks after the last induction treatment guinea pigs induced with the combination were challenged with 3 concentrations of the combination in distilled water (1000, 5000 and 15000 ppm a.i.), those induced with 886 were challenged with 3 concentrations of 886

TABLE 2

Calculation of Synergism of 573 and 651 Combinations

| Expt. No. | End-point Activity (MIC) in ppm | | | | Calculations | | | | | | | |
|---|---|---|---|---|---|---|---|---|---|---|---|---|
| | QA | QB | Qa | Qb | Total 573 Qa' | Total 651 Qb' | Total ppm Qa' + Qb' | % 573 | % 651 | Qa'/QA | Qb'/QB* | SI |
| 1 | 500 | 32 | 500.0 | 0 | 500.0 | 0.0 | 500.0 | 100.0 | 0.0 | 1.00 | 0.00 | 1.00 |
| | 500 | 32 | 250.0 | 1 | 250.2 | 0.7 | 251.0 | 99.7 | 0.3 | 0.50 | 0.03 | 0.53 |
| | 500 | 32 | 250.0 | 2 | 250.5 | 1.5 | 252.0 | 99.4 | 0.6 | 0.50 | 0.06 | 0.56 |
| | 500 | 32 | 125.0 | 2 | 125.5 | 1.5 | 127.0 | 98.8 | 1.2 | 0.25 | 0.06 | 0.31 |
| | 500 | 32 | 62.5 | 2 | 63.0 | 1.5 | 64.5 | 97.7 | 2.3 | 0.13 | 0.06 | 0.19 |
| | 500 | 32 | 31.2 | 2 | 31.7 | 1.5 | 33.2 | 95.5 | 4.5 | 0.06 | 0.06 | 0.13 |
| | 500 | 32 | 31.2 | 4 | 32.2 | 3.0 | 35.2 | 91.5 | 8.5 | 0.06 | 0.13 | 0.19 |
| | 500 | 32 | 31.2 | 8 | 33.2 | 6.0 | 39.2 | 84.7 | 15.3 | 0.07 | 0.25 | 0.32 |
| | 500 | 32 | 31.2 | 16 | 35.2 | 12.0 | 47.2 | 74.6 | 25.4 | 0.07 | 0.37 | 0.44 |
| | 500 | 32 | 15.6 | 16 | 19.6 | 12.0 | 31.6 | 62.1 | 37.9 | 0.04 | 0.50 | 0.54 |
| | 500 | 32 | 0.0 | 32 | 8.0 | 24.0 | 32.0 | 25.0 | 75.0 | 0.02 | 1.00 | 1.02 |
| 2 | 125 | 32 | 125.0 | 0 | 125.0 | 0.0 | 125.0 | 100.0 | 0.0 | 1.00 | 0.00 | 1.00 |
| | 125 | 32 | 62.5 | 1 | 62.7 | 0.7 | 63.5 | 98.8 | 1.2 | 0.50 | 0.03 | 0.53 |
| | 125 | 32 | 31.2 | 1 | 31.4 | 0.7 | 32.2 | 97.7 | 2.3 | 0.25 | 0.03 | 0.28 |
| | 125 | 32 | 31.2 | 2 | 31.7 | 1.5 | 33.2 | 95.5 | 4.5 | 0.25 | 0.06 | 0.31 |
| | 125 | 32 | 31.2 | 4 | 32.2 | 3.0 | 35.2 | 91.5 | 8.5 | 0.26 | 0.13 | 0.39 |
| | 125 | 32 | 31.2 | 8 | 33.2 | 6.0 | 39.2 | 84.7 | 15.3 | 0.27 | 0.25 | 0.52 |
| | 125 | 32 | 31.2 | 16 | 35.2 | 12.0 | 47.2 | 24.6 | 25.4 | 0.28 | 0.50 | 0.78 |
| | 125 | 32 | 0.0 | 32 | 8.0 | 24.0 | 32.0 | 25.0 | 75.0 | 0.06 | 1.00 | 1.06 |

QB* = QB × 75%

The new combination has a use rate of from 20 to 100 ppm and preferably from about 25 to about 50 ppm. It could be higher; however the possibility of sensitization would increase as the rate of use increases.

The percentage of 651 in the 573/651 combination which shows synergy is from 1.2 to 25.4% with the more preferred percentage of 651 in the combination of 573/651 being in the range of from about 2.3 to about 8.5% and the most preferred percentage of 651 in the combination of 573/651 being in the range of from about 2.3 to 4.5%.

These ranges of 651 are preferred (i.e. 2.3 to 8.5% and 2.3 to 4.5%) because they provide the lowest amounts of 651 and strongest synergy.

Sensitization Study

The study was conducted to determine the sensitization potential of the synergistic combination of 3.5% 651 and 96.5% 573. The results were compared to the in distilled water (100, 250 and 750 ppm a.i.) and those induced with 573 alone were challenged with 3 concentrations of 573 in distilled water (1000, 5000 and 15000 ppm a.i.). Twenty-four (24) and 48 hr after the challenge doses, the application sites were examined for erythema reactions and graded from 0 to 3 in accordance with a pre-established scoring system. Reactions graded 1 or greater were judged to be skin sensitization reactions.

No erythema was observed in the naive control group following challenge with 15000 ppm a.i. of the combination, 750 ppm a.i. 886 and 15000 ppm a.i. 573—the highest concentrations of each test material used for challenge (Table 1). In guinea pigs induced with the combination at concentrations of 1000 to 10000 ppm a.i. erythema responses were observed following challenge with 5000 and 15000 ppm a.i. of the combination (2/10 to 7/10 incidence), but not with 1000 ppm a.i. Animals induced with 15000 ppm a.i. of the combination exhibited a minimal response at 1000 ppm a.i. challenge (1/10), as well as, responses at 5000 and 15000 ppm a.i. challenge (4/10 and 7/10, respectively).

In guinea pigs induced with 886 biocide at 250 ppm, erythema responses were observed at 250 and 750 ppm a.i. challenge (1/10 and 4/10, respectively), but not at 100 ppm a.i. challenge. Animals induced with 886 at 500 and 750 ppm a.i. exhibited positive responses following challenge with 100, 250 and 750 ppm a.i. of biocide (1/10 to 6/10 incidence), except with those animals induced and challenged with 750 and 250 ppm a.i., respectively.

In guinea pigs induced with 573 at 5000 and 15000 ppm a.i., no erythema was observed following challenge with 1000 ppm a.i. 573 and a minimal to low incidence of erythema responses were observed following challenge with 5000 and 15000 ppm a.i. 573 (i.e., 1/10 to 3/10 incidence). Animals induced with 30000 ppm a.i. 573, exhibited a minimal to low incidence of erythema at all challenge concentrations of 573 (1/9 to 3/9).

A comparison of the sensitization potential of the synergistic combination to that of 886 suggests that the combination is 1/20 to 1/15 times as potent a sensitizer as 886. A statistical procedure was used to compare the incidence and severity of the responses in animals induced (5000, 10000 and 15000 ppm a.i.) and challenged (15000 ppm a.i.) with the combination to that in animals induced (250, 500 and 750 ppm a.i.) and challenged (750 ppm a.i.) with 886. The distribution of skin reaction scores in the 886 induction groups was not statistically different (p<0.20) from that in the synergistic combination induction groups (i.e., at 20 times higher concentrations) following challenge with the highest doses. Likewise, the sensitization potential of the 573 combination was approximately ⅓ to ½ that of the combination (i.e., at 5000 and 15000 ppm induction and 1000, 5000 and 15000 ppm challenge for each test material, the overall incidence was 23 out of a possible 60 responses versus 7 out of a possible 60 responses for the synergistic combination and 573, respectively).

In conclusion, the synergistic combination produced delayed contact hypersensitivity in guinea pigs, but the sensitization potential of this test combination is 1/20 to 1/15 that of 886.

TABLE 3

Erythema Responses of 1 or Greater at 24 and/or 48 Hours

| Induction Phase[a] | | Challenge Phase[b] | | |
|---|---|---|---|---|
| Treatment | Dose (ppm) | Synergistic Combination 15000 ppm | 886 750 ppm | 573 15000 ppm |
| Naive Control[c] | — | 0/10 | 0/10 | 0/10 |

| | | Synergistic Combination | | |
|---|---|---|---|---|
| Treatment | Dose (ppm) | 1000 ppm | 5000 ppm | 15000 ppm |
| Synergistic Combination | 1000 | 0/10 | 2/10 | 2/10 |
| Synergistic Combination | 5000 | 0/10 | 4/10 | 7/10 |
| Synergistic Combination | 10000 | 0/10 | 3/10 | 6/10 |
| Synergistic Combination | 15000 | 1/10 | 4/10 | 7/10 |

| Treatment | Dose (ppm) | 886 100 ppm | 886 250 ppm | 886 750 ppm |
|---|---|---|---|---|
| 886 | 250 | 0/10 | 1/10 | 4/10 |
| 886 | 500 | 1/10 | 2/10 | 6/10 |
| 886 | 750 | 2/10 | 0/10 | 6/10 |

| Treatment | Dose (ppm) | 573 1000 ppm | 573 5000 ppm | 573 15000 ppm |
|---|---|---|---|---|
| 573 | 5000 | 0/10 | 1/10 | 2/10 |
| 573 | 15000 | 0/10 | 1/10 | 3/10 |
| 573 | 30000 | 1/9 | 2/9 | 3/9 |

[a]Guinea pigs received ten (6 hr.) induction exposures of the ten materials (0.4 ml per exposure) over a 22 day period.
[b]All guinea pigs received 0.4 ml of challenge doses as specified two weeks after the last induction dose.
[c]Guinea pigs received sham treatment only.

What is claimed:

1. A microbicidal composition comprising a synergistic mixture the first component of which is in the range of from about 1.2 to 25.4% of 5-chloro-2-methyl-4-isothiazolin-3-one and the second component of which is in the range of from about 74.6 to about 98.8% of 2-methyl-4-isothiazolin-3-one.

2. The microbicidal composition of claim 1 wherein the 5-chloro-2-methyl-4-isothiazolin-3-one is in the range of from about 2.3 to 8.5% and the 2-methyl-4-isothiazolin-3-one is in the range of from about 91.5 to about 97.7%.

3. The microbicidal composition of claim 2 wherein the 5-chloro-2-methyl-4-isothiazolin-3-one is in the range of from about 2.3 to about 4.5% and the 2-methyl-4-isothiazolin3-one is in the range of from about 95.5 to about 97.7%.

* * * * *